US009563268B2

(12) United States Patent
Smith et al.

(10) Patent No.: US 9,563,268 B2

(45) Date of Patent: Feb. 7, 2017

(54) HEART RATE CONTROL BASED UPON MEDIA CONTENT SELECTION

(71) Applicant: Spotify AB, Stockholm (SE)

(72) Inventors: Owen Smith, Stockholm (SE); Sten Garmark, Stockholm (SE); Gustav Söderström, Ekerö (SE)

(73) Assignee: Spotify AB, Stockholm (SE)

(*) Notice: Subject to any disclaimer, the term of this patent is extended or adjusted under 35 U.S.C. 154(b) by 0 days.

(21) Appl. No.: 14/883,245

(22) Filed: Oct. 14, 2015

(65) Prior Publication Data

US 2016/0342199 A1 Nov. 24, 2016

Related U.S. Application Data

(60) Provisional application No. 62/163,915, filed on May 19, 2015.

(51) Int. Cl.

| | |
|---|---|
| ***G06F 17/00*** | (2006.01) |
| ***G06F 3/01*** | (2006.01) |
| ***G06F 3/16*** | (2006.01) |
| ***A61B 5/024*** | (2006.01) |
| ***A63B 71/00*** | (2006.01) |

(52) U.S. Cl.

CPC ............... *G06F 3/011* (2013.01); *A61B 5/024* (2013.01); *A63B 71/00* (2013.01); *G06F 3/165* (2013.01); *A63B 2230/062* (2013.01)

(58) Field of Classification Search

CPC ............ A63B 69/0028; A63B 2225/20; A63B 71/0686; G06F 17/30743; G06F 17/30764; G10H 1/40; G10H 2210/381; G10H 2220/201; G10H 2240/131; G11B 27/105

See application file for complete search history.

(56) References Cited

U.S. PATENT DOCUMENTS

| | | | | |
|---|---|---|---|---|
| 7,737,353 | B2 | 6/2010 | Sasaki et al. | |
| 8,101,843 | B2 | 1/2012 | Turner | |
| 8,254,829 | B1 | 8/2012 | Kindred et al. | |
| 8,392,007 | B1 * | 3/2013 | Izo | G06F 3/165 455/3.06 |
| 2005/0126370 | A1 | 6/2005 | Takai et al. | |
| 2006/0107822 | A1 | 5/2006 | Bowen | |

(Continued)

FOREIGN PATENT DOCUMENTS

| | | |
|---|---|---|
| JP | 2012022242 A | 2/2012 |
| WO | 2010/010830 A1 | 1/2010 |

OTHER PUBLICATIONS

Nishitani, Machine generated translation of JP 2012022242 A, published Feb. 2, 2012.

(Continued)

*Primary Examiner* — Fan Tsang
*Assistant Examiner* — Eugene Zhao
(74) *Attorney, Agent, or Firm* — Merchant & Gould P.C.

(57) ABSTRACT

A media-playback device includes: a media-output device that plays media content items; a physiological measurement device programmed to measure at least one physiological measurement of a user of the media-output device; and a physiological control engine configured to: identify a current physiological measurement for the user; and cause the media-output device to modify playback of the media content items based upon the current physiological measurement.

13 Claims, 7 Drawing Sheets

(56) References Cited

U.S. PATENT DOCUMENTS

| | | | |
|---|---|---|---|
| 2006/0169125 | A1 | 8/2006 | Ashkenazi et al. |
| 2006/0288846 | A1 | 12/2006 | Logan |
| 2007/0060446 | A1* | 3/2007 | Asukai ............... A63B 24/0021 482/8 |
| 2007/0074617 | A1 | 4/2007 | Vergo |
| 2007/0074618 | A1 | 4/2007 | Vergo |
| 2007/0074619 | A1 | 4/2007 | Vergo |
| 2007/0079691 | A1 | 4/2007 | Turner |
| 2007/0169614 | A1* | 7/2007 | Sasaki ................ A63B 69/0028 84/612 |
| 2007/0203421 | A1 | 8/2007 | Cho et al. |
| 2007/0291958 | A1 | 12/2007 | Jehan |
| 2008/0096726 | A1 | 4/2008 | Riley et al. |
| 2008/0153671 | A1* | 6/2008 | Ogg ................... A63B 71/0686 482/3 |
| 2009/0231964 | A1 | 9/2009 | Kraft et al. |
| 2010/0031805 | A1 | 2/2010 | Fratti et al. |
| 2010/0188405 | A1 | 7/2010 | Haughay, Jr. et al. |
| 2010/0210421 | A1* | 8/2010 | Case, Jr. ................ A63B 24/00 482/8 |
| 2012/0254907 | A1 | 10/2012 | Serdiuk |
| 2013/0263049 | A1 | 10/2013 | Lehtiniemi et al. |
| 2014/0180762 | A1 | 6/2014 | Gilbert |
| 2014/0188638 | A1 | 7/2014 | Jones et al. |
| 2014/0222830 | A1 | 8/2014 | Ringer et al. |
| 2014/0338516 | A1 | 11/2014 | Andri |
| 2015/0081066 | A1 | 3/2015 | Yeh et al. |
| 2015/0142147 | A1 | 5/2015 | Stanghed et al. |
| 2015/0181314 | A1 | 6/2015 | Swanson |

OTHER PUBLICATIONS

U.S. Appl. No. 14/883,252, filed Oct. 14, 2015 for "Repetitive Motion Activity Enhancement Based Upon Media Content Selection".

U.S. Appl. No. 14/883,340, filed Oct. 14, 2015 for "Cadence-Based Selection, Playback, and Transition Between Song Versions".

U.S. Appl. No. 14/883,232, filed Oct. 14, 2015 for "Cadence Determination and Media Content Selection".

U.S. Appl. No. 14/883,298, filed Oct. 14, 2015 for "Cadence-Based Playlists Management System".

U.S. Appl. No. 14/883,273, filed Oct. 14, 2015 for "Multi-Track Playback of Media content During Repetitive Motion Activities".

U.S. Appl. No. 14/883,295, filed Oct. 14, 2015 for "Search Media Content Based Upon Tempo".

U.S. Appl. No. 14/883,318, filed Oct. 14, 2015 for "Cadence and Media Content Phase Alignment".

U.S. Appl. No. 14/944,972, filed Nov. 18, 2015 for "System for Managing Transitions Between Media Content Items".

U.S. Appl. No. 14/945,008, filed Nov. 18, 2015 for "Identifying Media Content".

U.S. Appl. No. 14/883,323, filed Oct. 14, 2015 for "Accessibility Management System for Media Content Items".

U.S. Appl. No. 14/883,336, filed Oct. 14, 2015 for "Selection and Playback of Song Versions Using Cadence".

The Echonest, "Analyzer Documentation", Version 32, Jan. 7, 2014, 7 pages.

* cited by examiner

HEART RATE CONTROL BASED UPON MEDIA CONTENT SELECTION

CROSS-REFERENCE TO RELATED APPLICATION

This application claims priority to U.S. Ser. No. 62/163,915, filed May 19, 2015 entitled HEART RATE CONTROL BASED UPON MEDIA CONTENT SELECTION, the disclosure of which is hereby incorporated by reference in its entirety.

BACKGROUND

Running, as well as many other recreation or fitness activities, include repetitive motions. For example, running and walking involve repetitive steps, biking involves repetitive rotational movements, rowing involves repetitive strokes, and swimming involves repetitive strokes and kicks. There are of course many other recreation and fitness activities that also include various repetitive motions. These repetitive motion activities may be performed in place (e.g., using a treadmill, stationary bike, rowing machine, swimming machine, etc.) or in motion (e.g., on roads, trails, or tracks or in a pool or body of water, etc.). Cadence refers to the frequency of these repetitive motions and is often measured in terms of motions per minute (e.g., steps per minute, rotations per minute, strokes per minute, or kicks per minute).

Many people enjoy consuming media content, such as listening to audio content or watching video content, while running or engaging in other repetitive-motion activities. Examples of audio content include songs, albums, podcasts, audiobooks, etc. Examples of video content include movies, music videos, television episodes, etc. Using a mobile phone or other media-playback device a person can access large catalogs of media content. For example, a user can access an almost limitless catalog of media content through various free and subscription-based streaming services. Additionally, a user can store a large catalog of media content on his or her mobile device.

This nearly limitless access to media content introduces new challenges for users. For example, it may be difficult to find or select the right media content that complements a particular moment during a run or other repetitive-motion activity.

SUMMARY

In general terms, this disclosure is directed to the selection and/or control of media content based upon one or more physiological attributes. Various aspects are described in this disclosure, which include, but are not limited to, the following aspects.

In one aspect, a media-playback device includes: a media-output device that plays media content items; a physiological measurement device programmed to measure at least one physiological measurement of a user of the media-output device; and a physiological control engine configured to: identify a current physiological measurement for the user; and cause the media-output device to modify playback of the media content items based upon the current physiological measurement.

In another aspect, a media-playback device includes: a media-output device that plays media content items; a physiological measurement device programmed to measure a heart rate of a user of the media-output device; and a physiological control engine configured to: identify a current heart rate for the user; and cause the media-output device to modify a tempo of the media content items based upon the current heart rate.

In yet another aspect, a method for media-playback includes: playing media content items; measuring a heart rate of a user; identifying a current heart rate of the user; and modifying a tempo of the media content items based upon the current heart rate.

DETAILED DESCRIPTION

Figure 1:
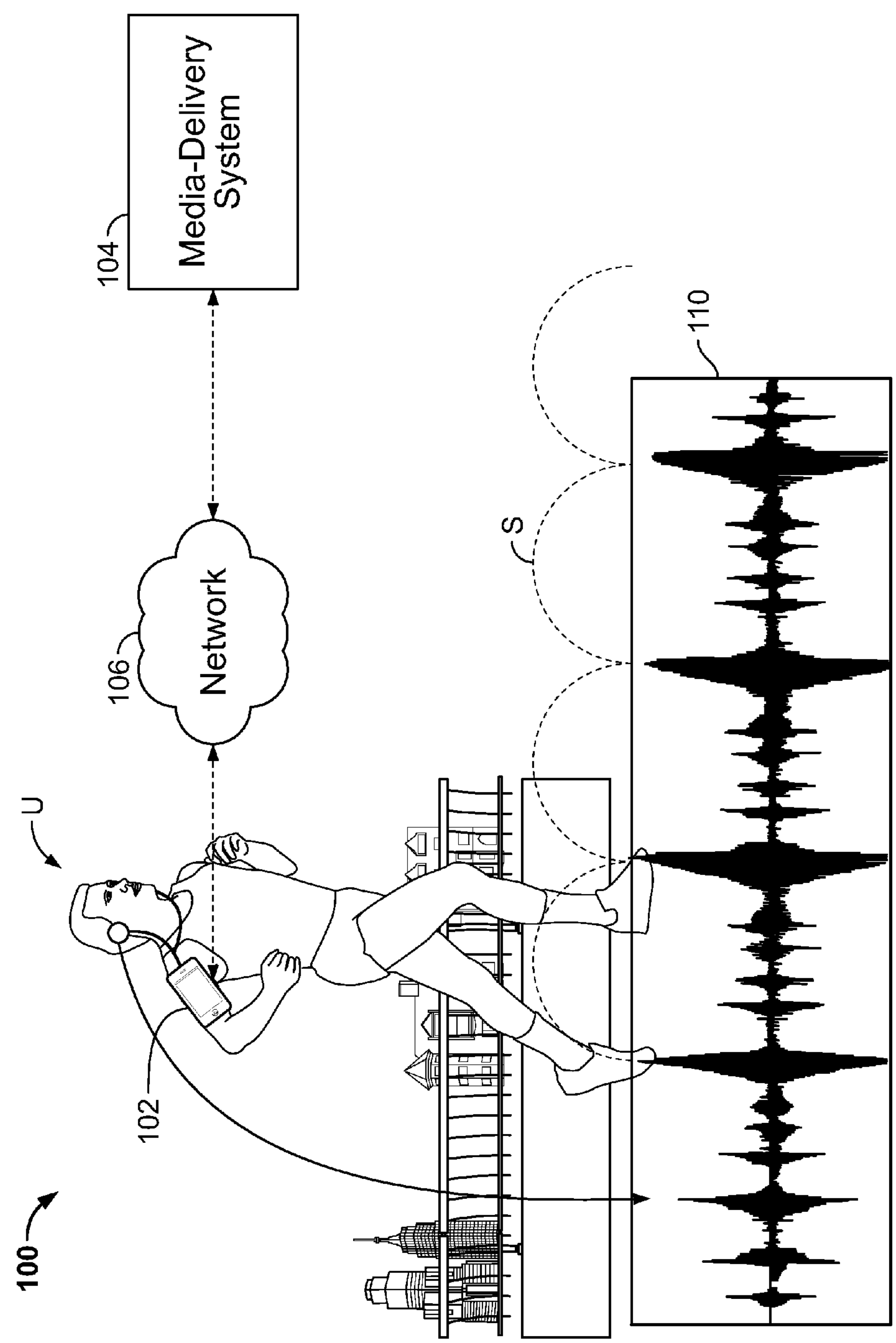
FIG. 1 illustrates an example system for heart rate determination and media content selection.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

Users of media-playback devices often consume media content while engaging in various activities, including repetitive motion activities. As noted above, examples of repetitive-motion activities may include swimming, biking, running, rowing, and other activities. Consuming media content may include one or more of listening to audio content, watching video content, or consuming other types of media content. For ease of explanation, the embodiments described in this application are presented using specific examples. For example, audio content (and in particular music) is described as an example of one form of media consumption. As another example, running is described as one example of a repetitive-motion activity. However, it should be understood that the same concepts are equally applicable to other forms of media consumption and to other forms of repetitive-motion activities, and at least some embodiments include other forms of media consumption and/or other forms of repetitive-motion activities.

The users may desire that the media content fits well with the particular repetitive-motion activity. For example, a user who is running may desire to listen to music with a beat that corresponds to the user's cadence. Beneficially, by matching the beat of the music to the cadence, the user's performance or enjoyment of the repetitive-motion activity may be enhanced. This desire cannot be met with traditional media-playback devices and media-delivery systems.

FIG. 1 illustrates an example system 100 for cadence determination and media content selection. The example system 100 includes a media-playback device 102 and a media-delivery system 104. The system 100 communicates across a network 106. Also shown, is a user U who is running. The user U's upcoming steps S are shown as well. A step represents a single strike of the runner's foot upon the ground.

The media-playback device 102 operates to play media content items to produce media output 110. In some embodiments, the media content items are provided by the media-delivery system 104 and transmitted to the media-playback device 102 using the network 106. A media content item is an item of media content, including audio, video, or other types of media content, which may be stored in any format suitable for storing media content. Non-limiting examples of media content items include songs, albums, music videos, movies, television episodes, podcasts, other types of audio or video content, and portions or combinations thereof.

The media-playback device 102 plays media content for the user based on the user's cadence. In the example shown, the media output 110 includes music with a tempo that corresponds to the user's cadence. The tempo (or rhythm) of music refers to the frequency of the beat and is typically measured in beats per minute (BPM). The beat is the basic unit of rhythm in a musical composition (as determined by the time signature of the music). Accordingly, in the example shown, the user U's steps occur at the same frequency as the beat of the music.

For example, if the user U is running at a cadence of 180 steps per minute, the media-playback device 102 may play a media content item having a tempo equal to or approximately equal to 180 BPM. In other embodiments, the media-playback device 102 plays a media content item having a tempo equal or approximately equal to the result of dividing the cadence by an integer such as a tempo that is equal to or approximately equal to one-half (e.g., 90 BPM when the user is running at a cadence of 180 steps per minute), one-fourth, or one-eighth of the cadence. Alternatively, the media-playback device 102 plays a media content item having a tempo that is equal or approximately equal to an integer multiple (e.g., 2×, 4×, etc.) of the cadence. Further, in some embodiments, the media-playback device 102 operates to play multiple media content items including one or more media content items having a tempo equal to or approximately equal to the cadence and one or more media content items have a tempo equal or approximately equal to the result of multiplying or dividing the cadence by an integer. Various other combinations are possible as well.

In some embodiments, the media-playback device 102 operates to play music having a tempo that is within a predetermined range of a target tempo. In at least some embodiments, the predetermined range is plus or minus 2.5 BPM. For example, if the user U is running at a cadence of 180 steps per minute, the media-playback device 102 operates to play music having a tempo of 177.5-182.5 BPM. Alternatively, in other embodiments, the predetermined range is itself in a range from 1 BPM to 10 BPM.

Further, in some embodiments, the media-playback device 102 operates to play music having a tempo equal to or approximately equal to a user U's cadence after it is rounded. For example, the cadence may be rounded to the nearest multiple of 2.5, 5, or 10 and then the media-playback device 102 plays music having a tempo equal to or approximately equal to the rounded cadence. In yet other embodiments, the media-playback device 102 uses the cadence to select a predetermined tempo range of music for playback. For example, if the user U's cadence is 181 steps per minute, the media-playback device 102 may operate to play music from a predetermined tempo range of 180-184.9 BPM; while if the user U's cadence is 178 steps per minute, the media-playback device 102 may operate to play music from a predetermined tempo range of 175-179.9 BPM.

Figure 2:
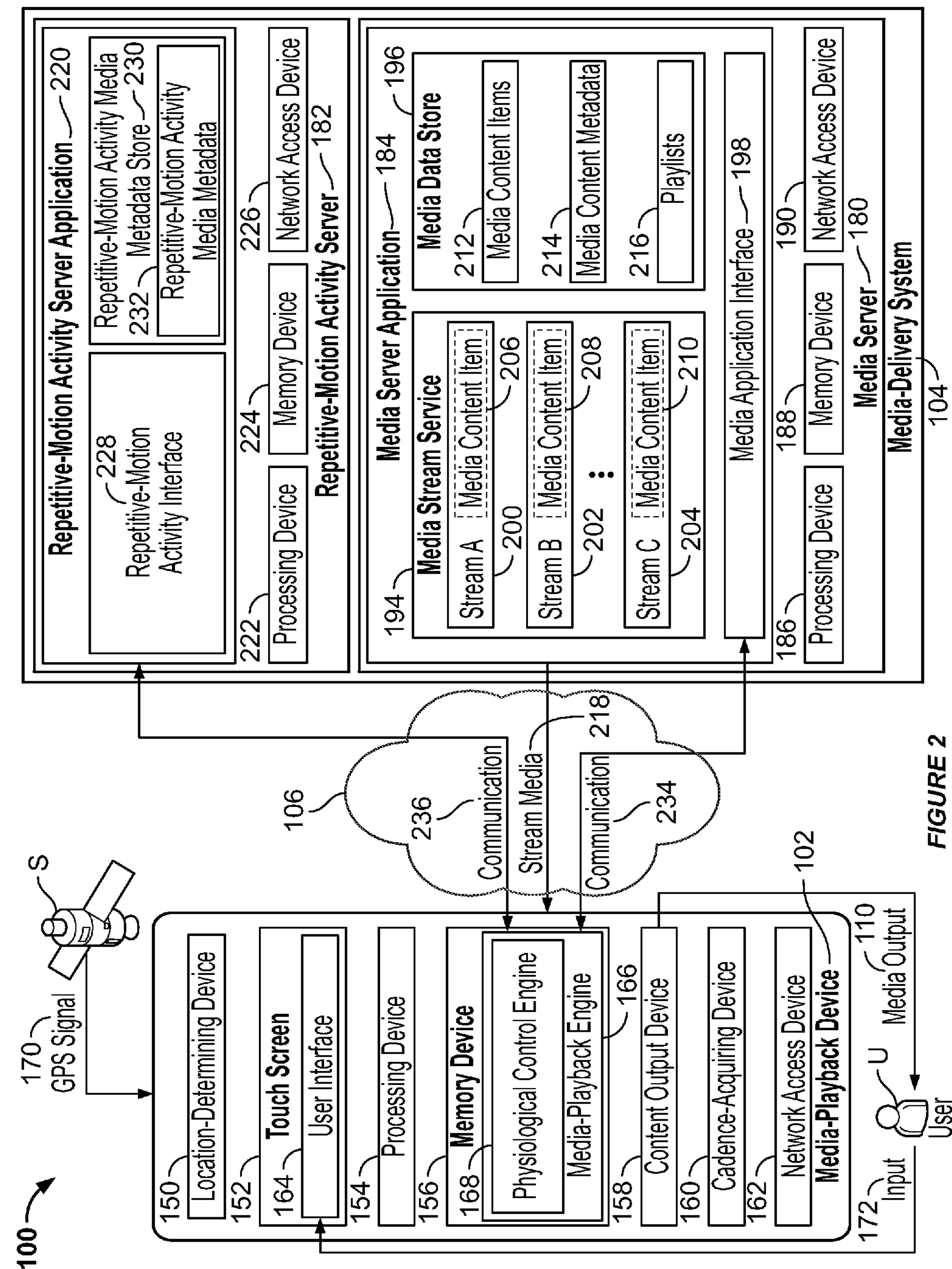
FIG. 2 is a schematic illustration of the example system of FIG. 1.

FIG. 2 is a schematic illustration of an example system 100 for cadence determination and media content selection. In FIG. 2, the media-playback device 102, the media-delivery system 104, and the network 106 are shown. Also shown are the user U and a satellite S.

As noted above, the media-playback device 102 operates to play media content items. In some embodiments, the media-playback device 102 operates to play media content items that are provided (e.g., streamed, transmitted, etc.) by a system external to the media-playback device such as the media-delivery system 104, another system, or a peer device. Alternatively, in some embodiments, the media-playback device 102 operates to play media content items stored locally on the media-playback device 102. Further, in at least some embodiments, the media-playback device 102 operates to play media content items that are stored locally as well as media content items provided by other systems.

In some embodiments, the media-playback device 102 is a computing device, handheld entertainment device, smartphone, tablet, watch, wearable device, or any other type of device capable of playing media content. In yet other embodiments, the media-playback device 102 is a laptop computer, desktop computer, television, gaming console, set-top box, network appliance, blue-ray or DVD player, media player, stereo, or radio.

In at least some embodiments, the media-playback device 102 includes a location-determining device 150, a touch screen 152, a processing device 154, a memory device 156, a content output device 158, a cadence-acquiring device 160, and a network access device 162. Other embodiments may include additional, different, or fewer components. For example, some embodiments may include a recording device such as a microphone or camera that operates to record audio or video content. As another example, some embodiments do not include one or more of the location-determining device 150 and the touch screen 152.

The location-determining device 150 is a device that determines the location of the media-playback device 102. In some embodiments, the location-determining device 150 uses one or more of the following technologies: Global Positioning System (GPS) technology which may receive GPS signals 170 from satellites S, cellular triangulation technology, network-based location identification technology, Wi-Fi positioning systems technology, and combinations thereof.

The touch screen 152 operates to receive an input 172 from a selector (e.g., a finger, stylus etc.) controlled by the user U. In some embodiments, the touch screen 152 operates as both a display device and a user input device. In some embodiments, the touch screen 152 detects inputs based on one or both of touches and near-touches. In some embodiments, the touch screen 152 displays a user interface 164 for interacting with the media-playback device 102. As noted above, some embodiments do not include a touch screen 152. Some embodiments include a display device and one or more separate user interface devices. Further, some embodiments do not include a display device.

In some embodiments, the processing device 154 comprises one or more central processing units (CPU). In other embodiments, the processing device 154 additionally or alternatively includes one or more digital signal processors, field-programmable gate arrays, or other electronic circuits.

The memory device 156 operates to store data and instructions. In some embodiments, the memory device 156 stores instructions for a media-playback engine 166 that includes a physiological control engine 168. In some embodiments, the media-playback engine 166 operates to playback media content and the physiological control engine 168 operates to select media content for playback based on various conditions, such as physiological measurements like heart rate, etc. and/or current location. Additional details regarding the physiological control engine 168 are provided below.

The memory device 156 typically includes at least some form of computer-readable media. Computer readable media includes any available media that can be accessed by the media-playback device 102. By way of example, computer-readable media include computer readable storage media and computer readable communication media.

Computer readable storage media includes volatile and nonvolatile, removable and non-removable media implemented in any device configured to store information such as computer readable instructions, data structures, program modules, or other data. Computer readable storage media includes, but is not limited to, random access memory, read only memory, electrically erasable programmable read only memory, flash memory and other memory technology, compact disc read only memory, blue ray discs, digital versatile discs or other optical storage, magnetic cassettes, magnetic tape, magnetic disk storage or other magnetic storage devices, or any other medium that can be used to store the desired information and that can be accessed by the media-playback device 102. In some embodiments, computer readable storage media is non-transitory computer readable storage media.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The content output device 158 operates to output media content. In some embodiments, the content output device 158 generates media output 110 for the user U. Examples of the content output device 158 include a speaker, an audio output jack, a Bluetooth transmitter, a display panel, and a video output jack. Other embodiments are possible as well. For example, the content output device 158 may transmit a signal through the audio output jack or Bluetooth transmitter that can be used to reproduce an audio signal by a connected or paired device such as headphones or a speaker.

The cadence-acquiring device 160 operates to acquire a cadence associated with the user U. In at least some embodiments, the cadence-acquiring device 160 operates to determine cadence directly and includes one or more accelerometers or other motion-detecting technologies. Alternatively, the cadence-acquiring device 160 operates to receive data representing a cadence associated with the user U. For example, in some embodiments, the cadence-acquiring device 160 operates to receive data from a watch, bracelet, foot pod, chest strap, shoe insert, anklet, smart sock, bicycle computer, exercise equipment (e.g., treadmill, rowing machine, stationary cycle), or other device for determining or measuring cadence. Further, in some embodiments, the cadence-acquiring device 160 operates to receive a cadence value input by the user U or another person.

The network access device 162 operates to communicate with other computing devices over one or more networks, such as the network 106. Examples of the network access device include wired network interfaces and wireless network interfaces. Wireless network interfaces includes infrared, BLUETOOTH® wireless technology, 802.11a/b/g/n/ac, and cellular or other radio frequency interfaces in at least some possible embodiments.

The network 106 is an electronic communication network that facilitates communication between the media-playback device 102 and the media-delivery system 104. An electronic communication network includes a set of computing devices and links between the computing devices. The computing devices in the network use the links to enable communication among the computing devices in the network. The network 106 can include routers, switches, mobile access points, bridges, hubs, intrusion detection devices, storage devices, standalone server devices, blade server devices, sensors, desktop computers, firewall devices, laptop computers, handheld computers, mobile telephones, and other types of computing devices.

In various embodiments, the network 106 includes various types of links. For example, the network 106 can include wired and/or wireless links, including Bluetooth, ultra-wideband (UWB), 802.11, ZigBee, cellular, and other types of wireless links. Furthermore, in various embodiments, the network 106 is implemented at various scales. For example, the network 106 can be implemented as one or more local area networks (LANs), metropolitan area networks, subnets, wide area networks (such as the Internet), or can be implemented at another scale. Further, in some embodiments, the network 106 includes multiple networks, which may be of the same type or of multiple different types.

The media-delivery system 104 comprises one or more computing devices and operates to provide media content items to the media-playback devices 102 and, in some embodiments, other media-playback devices as well. The media-delivery system 104 includes a media server 180 and a repetitive-motion activity server 182. In at least some embodiments, the media server 180 and the repetitive-motion activity server 182 are provided by separate computing devices. In other embodiments, the media server 180 and the repetitive-motion activity server 182 are provided by the same computing devices. Further, in some embodiments, one or both of the media server 180 and the repetitive-motion activity server 182 are provided by multiple computing devices. For example, the media server 180 and the repetitive-motion activity server 182 may be provided by multiple redundant servers located in multiple geographic locations.

The media server 180 operates to transmit stream media 218 to media-playback devices such as the media-playback device 102. In some embodiments, the media server 180 includes a media server application 184, a processing device 186, a memory device 188, and a network access device 190. The processing device 186, memory device 188, and network access device 190 may be similar to the processing device 154, memory device 156, and network access device 162 respectively, which have each been previously described.

In some embodiments, the media server application 184 operates to stream music or other audio, video, or other forms of media content. The media server application 184 includes a media stream service 194, a media data store 196, and a media application interface 198. The media stream service 194 operates to buffer media content such as media content items 206, 208, and 210, for streaming to one or more streams 200, 202, and 204.

The media application interface 198 can receive requests or other communication from media-playback devices or other systems, to retrieve media content items from the media server 180. For example, in FIG. 2, the media application interface 198 receives communication 234 from the media-playback engine 166.

In some embodiments, the media data store 196 stores media content items 212, media content metadata 214, and playlists 216. The media data store 196 may comprise one or more databases and file systems. Other embodiments are possible as well. As noted above, the media content items 212 may be audio, video, or any other type of media content, which may be stored in any format for storing media content.

The media content metadata 214 operates to provide various information associated with the media content items 212. In some embodiments, the media content metadata 214 includes one or more of title, artist name, album name, length, genre, mood, era, etc. The playlists 216 operate to identify one or more of the media content items 212 and. In some embodiments, the playlists 216 identify a group of the media content items 212 in a particular order. In other embodiments, the playlists 216 merely identify a group of the media content items 212 without specifying a particular order. Some, but not necessarily all, of the media content items 212 included in a particular one of the playlists 216 are associated with a common characteristic such as a common genre, mood, or era.

The repetitive-motion activity server 182 operates to provide repetitive-motion activity-specific information about media content items to media-playback devices. In some embodiments, the repetitive-motion activity server 182 includes a repetitive-motion activity server application 220, a processing device 222, a memory device 224, and a network access device 226. The processing device 222, memory device 224, and network access device 226 may be similar to the processing device 154, memory device 156, and network access device 162 respectively, which have each been previously described.

In some embodiments, repetitive-motion activity server application 220 operates to transmit information about the suitability of one or more media content items for playback during a particular repetitive-motion activity. The repetitive-motion activity server application 220 includes a repetitive-motion activity interface 228 and a repetitive-motion activity media metadata store 230.

In some embodiments, the repetitive-motion activity server application 220 may provide a list of media content items at a particular tempo to a media-playback device in response to a request that includes a particular cadence value. Further, in some embodiments, the media content items included in the returned list will be particularly relevant for the repetitive motion activity in which the user is engaged (for example, if the user is running, the returned list of media content items may include only media content items that have been identified as being highly runnable).

The repetitive-motion activity interface 228 operates to receive requests or other communication from media-playback devices or other systems to retrieve information about media content items from the repetitive-motion activity server 182. For example, in FIG. 2, the repetitive-motion activity interface 228 receives communication 236 from the media-playback engine 166.

In some embodiments, the repetitive-motion activity media metadata store 230 stores repetitive-motion activity media metadata 232. The repetitive-motion activity media metadata store 230 may comprise one or more databases and file systems. Other embodiments are possible as well.

The repetitive-motion activity media metadata 232 operates to provide various information associated with media content items, such as the media content items 212. In some embodiments, the repetitive-motion activity media metadata 232 provides information that may be useful for selecting media content items for playback during a repetitive-motion activity. For example, in some embodiments, the repetitive-motion activity media metadata 232 stores runnability scores for media content items that correspond to the suitability of particular media content items for playback during running. As another example, in some embodiments, the repetitive-motion activity media metadata 232 stores timestamps (e.g., start and end points) that identify portions of a media content items that are particularly well-suited for playback during running (or another repetitive-motion activity).

Each of the media-playback device 102 and the media-delivery system 104 can include additional physical computer or hardware resources. In at least some embodiments, the media-playback device 102 communicates with the media-delivery system 104 via the network 106.

Although in FIG. 2 only a single media-playback device 102 and media-delivery system 104 are shown, in accordance with some embodiments, the media-delivery system 104 can support the simultaneous use of multiple media-playback devices, and the media-playback device can simultaneously access media content from multiple media-delivery systems. Additionally, although FIG. 2 illustrates a streaming media based system for cadence determination and media content selection, other embodiments are possible as well. For example, in some embodiments, the media-playback device 102 includes a media data store 196 and the media-playback device 102 is configured to perform cadence determination and media content selection without accessing the media-delivery system 104. Further in some embodiments, the media-playback device 102 operates to store previously streamed media content items in a local media data store.

In at least some embodiments, the media-delivery system 104 can be used to stream, progressively download, or otherwise communicate music, other audio, video, or other forms of media content items to the media-playback device 102 based on a cadence acquired by the cadence-acquiring device 160 of the media-playback device 102. In accordance with an embodiment, a user U can direct the input 172 to the user interface 164 to issue requests, for example, to playback media content corresponding to the cadence of a repetitive motion activity on the media-playback device 102.

Figure 3:
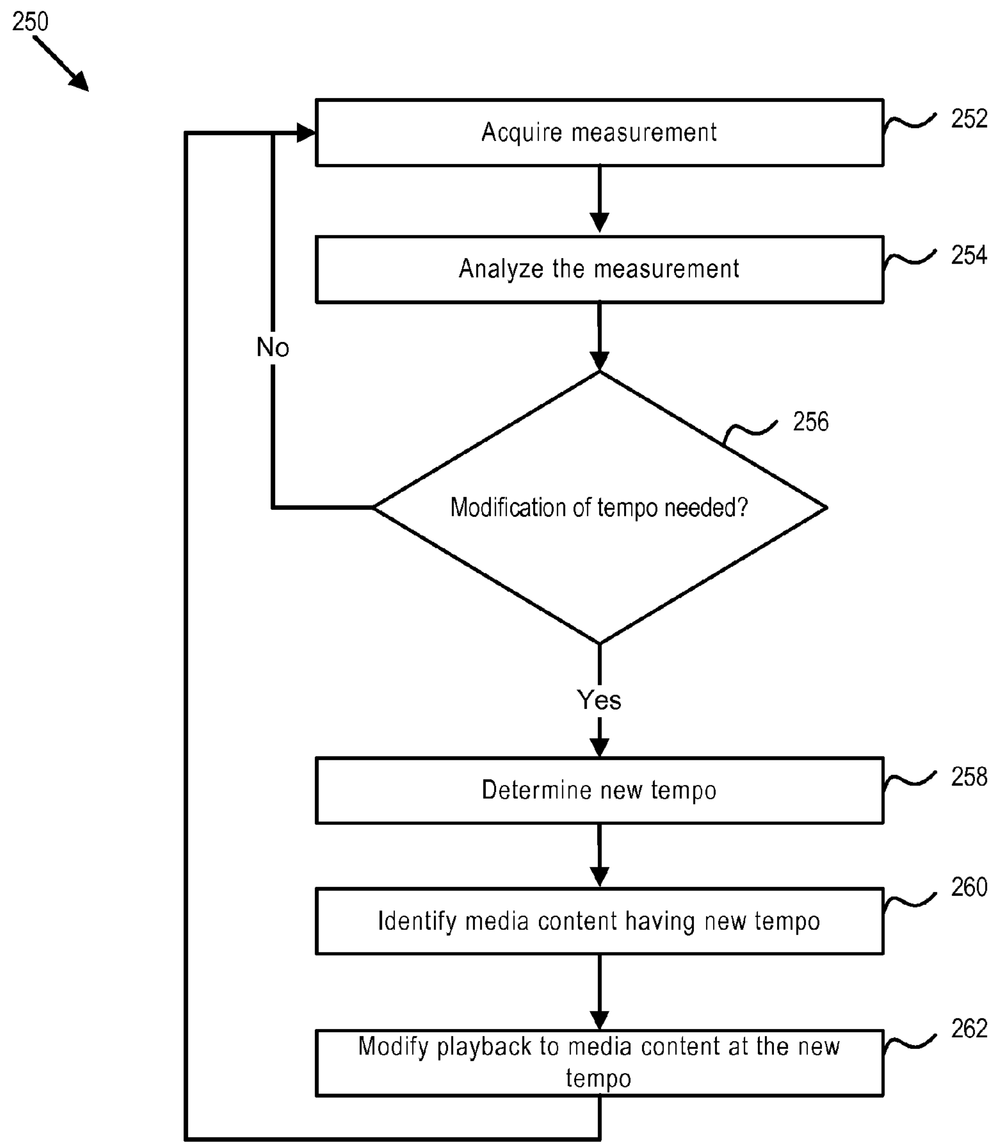
FIG. 3 illustrates an example method of modifying tempo based upon one or more physiological measurements obtained by some embodiments of the media-playback device of FIG. 1.

FIG. 3 illustrates an example method 250 of using an external measurement to control the tempo of the media content played by the media-playback device 102.

At step 252, a measurement is obtained by the media-playback device 102.

In some examples, this measurement includes one or more physiological measurements, such as the user U's heart rate (see FIGS. 4-6), respiration, temperature, sweat, stress, VO2, etc. In some examples, the physiological measurements can be obtained directly by the media-playback device 102 using a sensor 169. For example, if the media-playback device 102 is a watch, the watch can be configured with a heart rate sensor to approximate the heart rate of the user U. In other examples, one or more external sensors, such as a heart rate band worn around the torso, can be used to obtain the measurements. These measurements can be communicated to the media-playback device 102 using one or more known protocols, such as Bluetooth or ANT+ protocols.

Figure 6:
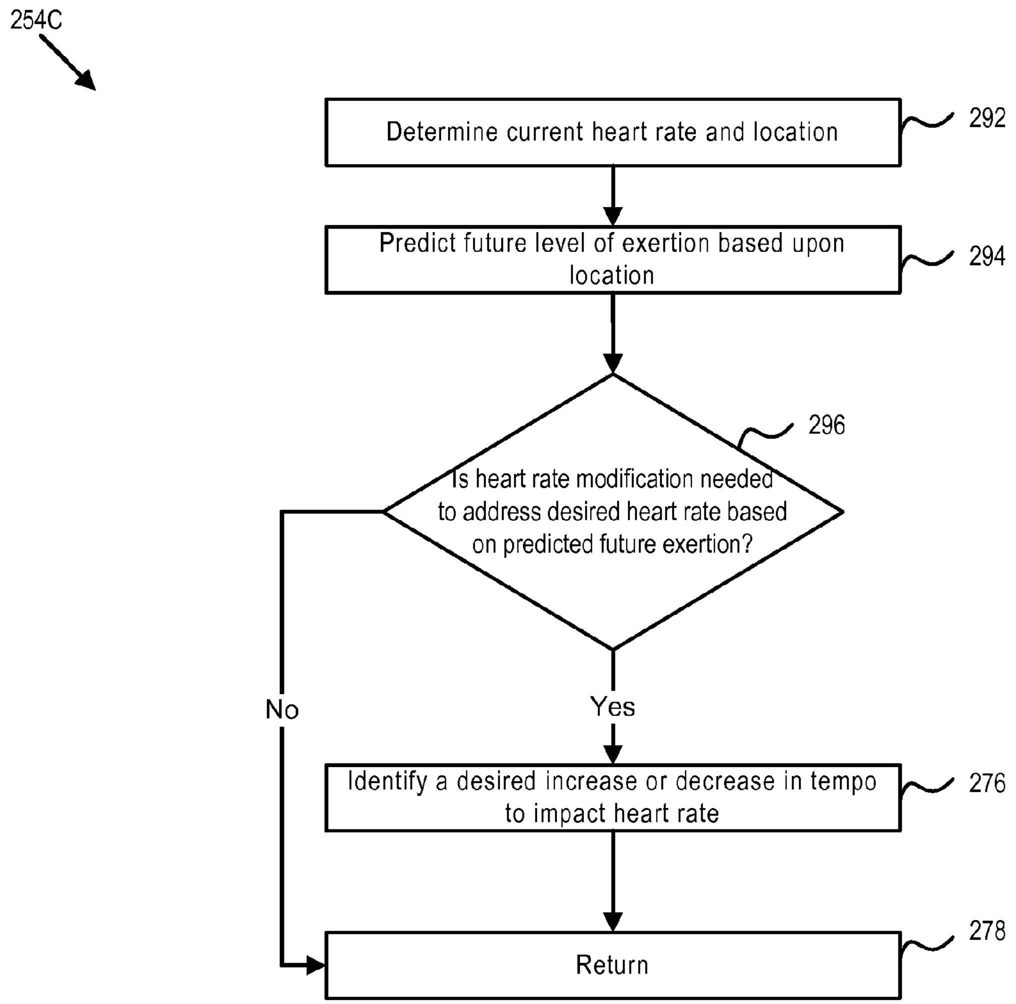
FIG. 6 illustrates another example method of modifying tempo based upon heart rate and current location obtained by some embodiments of the media-playback device of FIG. 1.

In other examples, the measurement can be a non-physiological measurement, such as the location of the user U (see FIG. 6). In these examples, the media-playback device 102 can directly provide the measurement (e.g., using the location-determining device 150 that receives GPS signals 170), or an external sensor can again be used.

At step 254, the measurement is analyzed. For example, as referred to in FIGS. 4-5, the physiological control engine 168 can be programmed to determine if the user U's heart rate is at a desired rate or too high/low. The user U's heart rate can be analyzed to determine if it falls within a desired range of rates.

At step 256, the media-playback device 102 analyzes the measurement to determine if a change in the tempo of the media content that is currently being played is needed to impact the measurement. For example, the tempo of the media content can be increased or decreased as noted below.

If the tempo does not need to be modified, control is passed back to step 252 and another measurement is acquired (e.g., in near real time or at periodic or manual intervals).

If the tempo does need to be modified, control is passed to operation 258, and the media-playback device 102 determines a new tempo for the media content being played. For example, if the physiological measurement is high or low, the media-playback device 102 can be programmed to increase or decrease the tempo of the media content in an attempt to impact the physiological measurement.

At step 260, media content having the new tempo is identified. In some examples, media content is categorized by tempo and can be accessed as desired to provide a certain tempo to encourage the user to maintain and/or increase/decrease the level of exertion through a maintenance or modification of the user's cadence. Examples of categorizing such media content is provided in U.S. Patent Application Ser. No. 62/163,887, titled MULTI-TRACK PLAYBACK OF MEDIA CONTENT DURING REPETITIVE MOTION ACTIVITIES, filed on May 19, 2015, the entirety of which is hereby incorporated by reference.

Finally, at step 262, the media-playback device 102 modifies playback to include the media content at the new tempo. In one example, the tempo of the media content that is currently being played by the media-playback device 102 can be modified (e.g., increased or decreased) to the new tempo. In another example, different media content having the new tempo can be played.

In some examples, the transition beat or beats between the current media content and the new media content are matched so that the user can maintain a steady cadence and transition increasing or decreasing the user U's cadence. Examples of how to match such beats is provided in U.S. Patent Application Ser. No. 62/163,910, titled REPETITIVE-MOTION ACTIVITY ENHANCEMENT BASED UPON MEDIA CONTENT SELECTION, filed on May 19, 2015, the entirety of which is hereby incorporated by reference.

Figure 4:
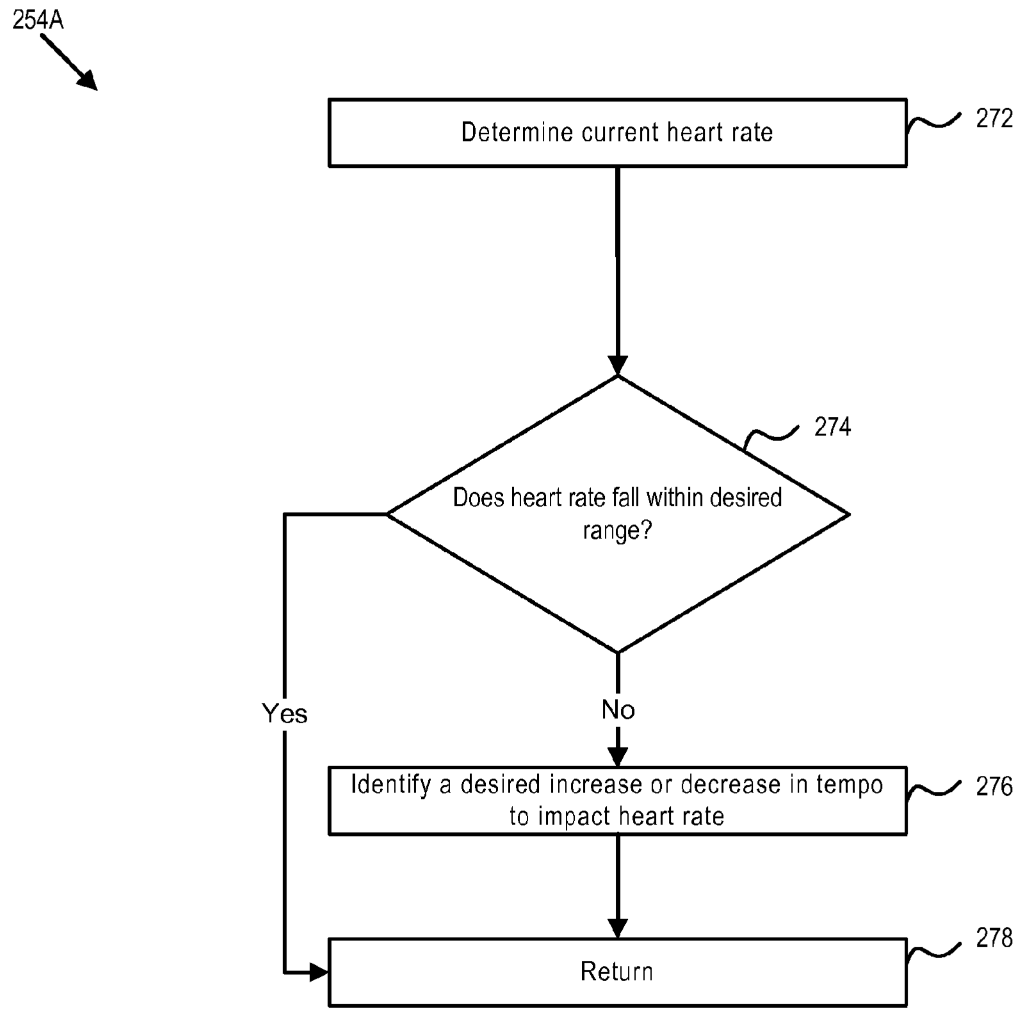
FIG. 4 illustrates an example method of modifying tempo based upon heart rate obtained by some embodiments of the media-playback device of FIG. 1.

Referring now to FIG. 4, an example method 254A is illustrated to show additional details about the step 254 of analyzing the measurement. In this example, the measurement is the heart rate of the user U, as measured by one or more sensors associated with the media-playback device 102, either directly or by, for example, a separate heart rate monitor device.

At step 272, the user U's current heart rate is determined from the measurements obtained from the sensor or sensors.

Next, at step 274, the media-playback device 102 determines if the heart rate falls within a desired range.

For example, many athletes train at a desired intensity. This intensity is commonly measured or approximated by analyzing the athlete's heart rate. The athlete may desire to keep his or her heart rate a certain level, such as below the anaerobic threshold for the athlete. In another example, the athlete may desire to keep the athlete's heart rate within a certain minimum or maximum thresholds, sometimes referred to as a particular heart rate zone.

The media-playback device 102 can be programmed to monitor these thresholds and determine if the user U's heart rate falls within the desired range. If so, control is passed to step 278, and control is returned to the method 250 described above.

If not, control is instead passed to operation 276, and the media-playback device 102 determines whether an increase or decrease in tempo may be desirable to impact the user U's heart rate.

For example, if the user U wishes to maintain his or her heart rate between 120 and 130 beats per minute, and the media-playback device 102 determines that the user U's heart rate is currently 115 beats per minute, the media-playback device 102 may determine that an increase in the tempo of the media content is desirable. This increase in the tempo of the media content is performed to assist or encourage the user U to increase the user U's intensity, such as cadence. This increased cadence can result in an increase in the user U's heart rate into the desired range.

Figure 5:
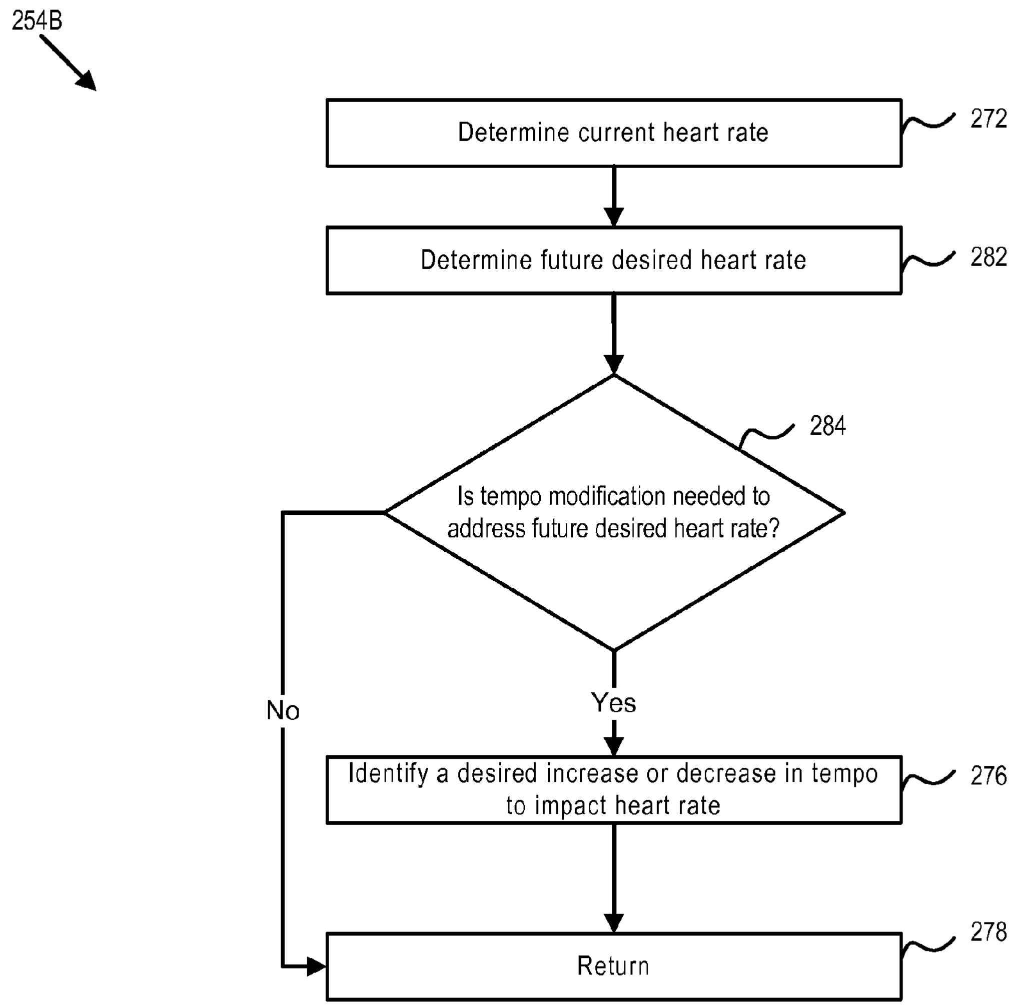
FIG. 5 illustrates another example method of modifying tempo based upon heart rate obtained by some embodiments of the media-playback device of FIG. 1.

Referring now to FIG. 5, another example of a method 254B is shown. The method 254B is similar to the method 254A described above, except at step 282 the media-playback device 102 compares the current heart rate of the user U to a future desired heart rate, such as a heart rate desired at a future point in time.

For example, the user U can define a workout plan that involves one or more changes in the user U's heart rate. For example, the user U can define a workout that requires the user U to maintain a first heart rate for a certain interval (e.g., 1 minute, 1 mile, etc.) and then to change that heart rate to a future heart rate for another interval.

The media-playback device 102 determines at step 284 when the future desired heart rate is approaching (e.g., when the user is close to a minute at the current heart rate) and starts to increase or decrease the tempo of the media content to assist the user in reaching the future heart rate at the desired time and/or distance. The workout plan for the user U can involve two or more heart rate changes, and the media-playback device 102 is programmed to assist the user U with those changes by shifting the media content to encourage the user U to increase or decrease the user U's cadence as needed to increase or decrease the user U's future heart rate.

At FIG. 6, another example of a method 254C is shown. The method 254C is similar to the method 254A described above, except at step 292 the media-playback device 102 determines both the heart rate and location of the user U. The location can be determined, for example, using the location-determining device 150.

Next, at step 294, the media-playback device 102 is programmed to estimate a future level of exertion for the user U based upon a future anticipated location of the user. For example, based upon the location, the media-playback device 102 can determine that the user U is approaching a hill. This determination can be made, for example, based upon elevation data accessed by the media-playback device 102 and the current direction of the user U and/or a pre-selected route provided by the user U.

When the media-playback device 102 determines that a hill is approaching based upon the location, a determination is made at step 296 as to whether or not the tempo of the media content should be modified in order to influence the performance of the user U.

For example, if the user U wishes to maintain a heart rate in a certain range, and the media-playback device 102 determines that a steep hill is approaching, the media-playback device 102 can select media content with a slower tempo to encourage the user U to slow his or her cadence as the hill approaches. This slower cadence will allow the user to maintain a lower heart rate as the user walks or runs up the hill.

In another example, if the media-playback device 102 determines that the user is approaching a downhill, the media-playback device 102 can increase the tempo of the media content that is playing to encourage an increase in cadence while maintaining the same heart rate, since the level of exertion for the user U will be less on the downhill.

Many alternatives are possible. For example, the user can program the media-playback device 102 to increase or decrease the tempo of the media content based upon location features (e.g., hills, etc.), the location itself (e.g., the user can have an increase in tempo during a certain stretch of a run to encourage increased cardiac output), and/or a combination of the current heart rate and location, as noted above.

In yet another example, multiple physiological measurements can be used to determine the current and future desired performance of the user. For example, both heart rate and respiration can be measured and the media content modified as desired to impact the heart rate and/or respiration of the user. Other configurations are possible.

Figure 7:
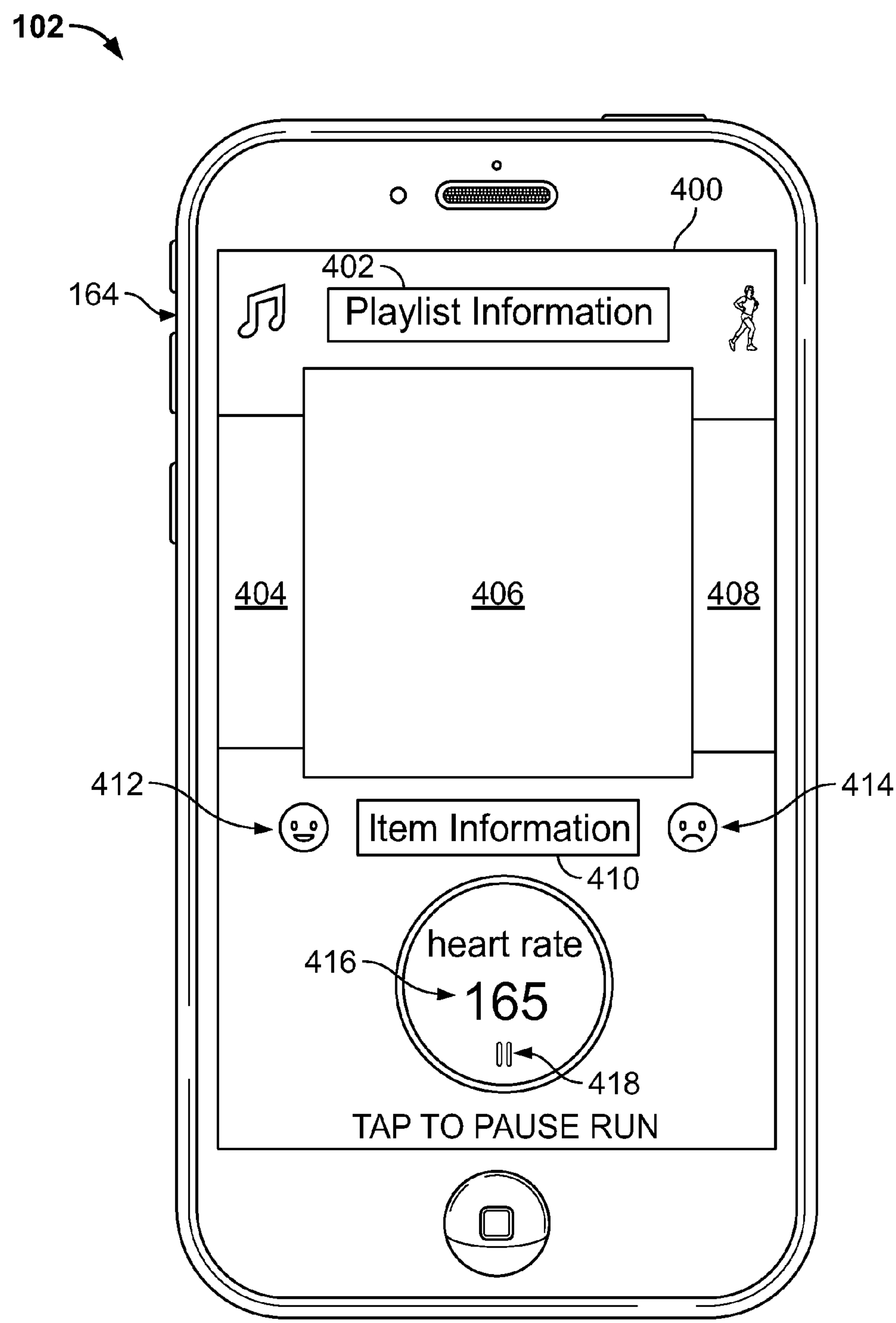
FIG. 7 is shows an example heart rate-based content playback screen displayed by some embodiments of the user interface of FIG. 2.

Referring now to FIG. 7, an example heart rate-based content playback screen 400 displayed by some embodiments of the user interface 164 of the media-playback device 102 is shown. In some embodiments, the heart rate-based content playback screen 400 is displayed in response to acquiring a heart rate of the user U associated with a user activity.

In some embodiments, the heart rate-based content playback screen 400 includes a playlist information message 402, a previous media content item display panel 404, a current media content item display panel 406, a next media content item display panel 408, a current media content item information message 410, a dislike control 412, a like control 414, a heart rate information message 416, and a pause control 418.

The playlist information message 402 operates to display information about the currently playing playlist of media content items. The playlist may be a pre-defined playlist of media content items that correspond to an acquired cadence or an ad-hoc playlist generated by the media-playback device 102 or the media-delivery system 104 based on the acquired cadence. In some embodiments, the playlist information message 402 displays a title provided with a pre-defined playlist (e.g. "Outdoor Running," "Spin Class," "Peak Performance," etc.). In some embodiments, the playlist information message 402 displays information that relates to the media content items included in an ad-hoc playlist such as a region (e.g., Sweden, Europe, U.S., etc.), a genre (e.g., Country, Rock, Rap, etc.), a mood (e.g., calm, happy, etc.), an era (e.g., 70's, 80's, 90's, 00's, etc.), or popularity (e.g., Top 50, etc.).

The previous media content item display panel 404 operates to display information about the previously played media content item such as an image associated with the previously played media content item (e.g., an album cover, an artist photograph, etc.). The current media content item display panel 406 and the next media content item display panel 408 operate similarly with respect to the currently playing media content item and the media content item that is schedule to play next. In some embodiments, the user interface 164 operates to cause the next or previous media content item to begin playback in response to detecting a swipe input to the left or right over the current media content item display panel 406. Additionally, in some embodiments, the user interface 164 operates to cause the previously played media content item to begin playback in response to detecting a touch input on the previous media content item display panel 404. Similarly, in some embodiments, the user interface 164 operates to cause the next media content item to begin playback in response to detecting a touch input on the next media content item display panel 408.

The current media content item information message 410 operates to display information about the currently playing media content item. Some embodiments display one or more of the following: a title, an artist name, an album name, a current position, a total length, and a tempo.

The dislike control 412 and the like control 414 operate to receive inputs indicating that a user dislikes or likes the currently playing media content item. In some embodiments, the media-playback device stores a like/dislike value associated with the currently playing media content item upon actuation of either the dislike control 412 or the like control 414. The value may be stored locally on the media-playback device 102 or remotely on the media-delivery system 104 or elsewhere. In some embodiments, one or both of the media-playback device 102 and the media-delivery system 104 use the like/dislike values that have been previously stored in selecting media content items for future playback. Additionally, in at least some embodiments, upon actuation of the dislike control 412, the currently playing media content item stops playing immediately or after a period of time and a new media content item begins to play.

The heart rate information message 416 operates to present information to the user about the acquired heart rate. In some embodiments, the heart rate information message 416 displays a numeric value representing the user U's current heart rate. Additionally, in some embodiments, the heart rate information message 416 also presents information related to whether the acquired heart rate has recently changed. For example, the heart rate information message 416 may include an arrow pointing up if the acquired heart rate has recently increased and an arrow pointing down if the acquired heart rate has recently decreased.

Alternatively, the heart rate may be displayed in a first color to indicate a recent increase, a second color to indicate a recent decrease, and a third color to indicate a stable heart rate. As yet another alternative, the heart rate information message 416 may blink or otherwise indicate the occurrence of a recent change in heart rate. In yet another embodiment, the heart rate information message 416 may operate to indicate how a currently acquired heart rate compares to a goal or target cadence using any of the previously mentioned visual indicators. Additionally, in some embodiments, the heart rate information message 416 operates to indicate if the media-playback device 102 has been unable to acquire a heart rate valued (e.g., an error has occurred, the heart rate sensor no longer reports a heart rate, etc.).

In yet other examples, information in addition to or other than heart rate can be displayed. For example, the information message 416 can be configured to display the tempo of the currently-playing media content item. In yet another example, the information message 416 can be configured to display an estimated cadence, as described in U.S. Patent Application Ser. No. 62/163,840, titled CADENCE DETERMINATION AND MEDIA CONTENT SELECTION, filed on May 19, 2015, the entirety of which is hereby incorporated by reference.

The pause control 418 operates to receive a pause input from the user. In some embodiments, the pause input triggers the media-playback device 102 to pause cadence acquisition. Beneficially, by pausing cadence acquisition, the user can take a break or otherwise change cadence without causing the playback of media content items to change. Users may take break for many reasons, such as to rest/recover, to wait to safely cross an intersection, or to wait for a running partner. Users may temporarily change cadence for many reasons as well such as to climb a stair case or a big hill, to cross rugged terrain, to weave through heavy traffic, etc. Additionally, in some embodiments, the pause input also triggers the media-playback device 102 to pause playback of the media content items.

As noted previously, although many of the examples provided above are described with respect to running, other embodiments relate to other repetitive motion activities as well such as cycling, swimming, and rowing.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following disclosure.

What is claimed is:

1. A media-playback device comprising:
- a media-output device that plays media content items;
- a physiological measurement device programmed to measure at least one physiological measurement of a user of the media-output device, the physiological measurement being associated with a level of exertion of the user during performance of a repetitive-motion activity;
- a location-determining device that is configured to determine a location of the media-playback device; and
- a physiological control engine configured to:
  - identify a current physiological measurement for the user;
  - determine a current location of the media-playback device;
  - use the current location to estimate a future level of exertion of the user and an estimated heart rate impact on the user based on an anticipated future location of the media-playback device; and
  - cause the media-output device to modify playback of the media content items to at least partially counteract the estimated heart rate impact based upon the current physiological measurement and the current location of the media playback device by adjusting a tempo used to select media content items for playback based on the estimated future level of exertion.

2. The device of claim 1, wherein the physiological control engine is configured to:
- compare the current physiological measurement to a range; and
- increase or decrease a tempo of the media content items based upon the comparison.

3. The device of claim 2, wherein the physiological control engine increases the tempo of the media content items when the current physiological measurement falls below the range.

4. The device of claim 3, wherein the current physiological measure is a current heart rate, and the range is a range of heart rates.

5. The device of claim 1, wherein the current physiological measure is a heart rate.

6. A media-playback device comprising:
- a media-output device that plays media content items;
- a physiological measurement device programmed to measure a heart rate of a user of the media-output device;
- a location-determining device that is configured to determine a location of the media-playback device; and
- a physiological control engine configured to:
  - identify a current heart rate for the user;
  - determine a current location of the media-playback device;
  - use the current location to estimate a future level of exertion of the user and an estimated heart rate impact on the user based on an anticipated future location of the media-playback device; and
  - cause the media-output device to modify a tempo of the media content items to at least partially counteract the estimated heart rate impact based upon the current heart rate and the current location of the media playback device by adjusting a tempo used to select media content items for playback based on the estimated future level of exertion.

7. The device of claim 6, wherein the physiological control engine is configured to:
- compare the current heart rate to a range; and
- increase or decrease the tempo of the media content items based upon the comparison.

8. The device of claim 7, wherein the physiological control engine increases the tempo of the media content items when the current heart rate falls below the range.

9. The device of claim 8, wherein the range is a range of heart rates.

10. A method performed by a media-playback device comprising:
- playing, by a media-output device, media content items;
- measuring, by a physiological measurement device, a heart rate of a user;
- identifying a current heart rate of the user;
- determining a current location of the user;
- using the current location to estimate a future level of exertion of the user and an estimated heart rate impact on the user based on an anticipated future location of the user; and
- modifying playback by the media-output device of the media content items to at least partially counteract the estimated heart rate impact based upon the current heart rate and the current location of the media playback device by adjusting a tempo used to select media content items for playback based on the estimated future level of exertion.

11. The method of claim 10, further comprising:

comparing the current heart rate to a range; and increasing or decreasing the tempo of the media content items based upon the comparison.

12. The method of claim 11, further comprising increasing the tempo of media content items when the current heart rate falls below the range.

13. The method of claim 12, wherein the range is a range of heart rates.

* * * * *